United States Patent
Buck

[11] Patent Number: 6,141,797
[45] Date of Patent: Nov. 7, 2000

[54] OPAQUE GOGGLES HAVING OPENABLE WINDOW

[76] Inventor: Robert Buck, One North St., Hastings-on-Hudson, N.Y. 10706

[21] Appl. No.: 09/298,525

[22] Filed: Apr. 23, 1999

[51] Int. Cl.⁷ ...................................................... A61F 9/02
[52] U.S. Cl. ........................ 2/15; 2/432; 2/453; 128/858; 351/46
[58] Field of Search ................................ 2/434, 432, 433, 2/439, 452, 453, 438, 441, 443, 15, 13; 351/45, 46; 128/858

[56] References Cited

U.S. PATENT DOCUMENTS

| | | | |
|---|---|---|---|
| 327,438 | 9/1885 | Fuller | 2/15 |
| 377,835 | 2/1888 | Lyman et al. | 2/15 |
| 562,071 | 6/1896 | De Moulin | 2/15 |
| 1,502,820 | 7/1924 | Funk | 2/453 |
| 2,271,703 | 2/1942 | McNeill | 2/453 |
| 2,907,041 | 10/1959 | Finn | 2/454 X |
| 3,555,563 | 1/1971 | Grossman | 351/46 X |
| 3,689,136 | 9/1972 | Atamian | 351/45 X |
| 5,372,504 | 12/1994 | Buechler | 2/13 X |
| 5,424,786 | 6/1995 | McCarthy | |
| 5,440,359 | 8/1995 | Bloch-Malem | 351/45 |
| 5,561,480 | 10/1996 | Capes | 351/45 |
| 5,963,294 | 10/1999 | Schiffer | 351/45 X |

FOREIGN PATENT DOCUMENTS 452266  8/1936  United Kingdom ........................ 2/453

OTHER PUBLICATIONS

Fredric Schiffer, M.D., "Of Two Minds" The Free Press, New York, 1998, pp. 56–57.

Primary Examiner—Peter Nerbun
Attorney, Agent, or Firm—Milde, Hoffberg & Macklin, LLP

[57] ABSTRACT

An improved pair of goggles capable of allowing one eye at a time to view things peripherally, which comprises: an opaque, translucent or tinted transparent front part of the goggles which fits in front of and covers the eyes of a wearer of the goggles, said front part having at least one window through which the wearer can view things by the outer periphery of the wearer's field of vision, a cover for the window which is capable of selectively covering the window or allowing the wearer to view things and a part that allows the wearer to wear the goggles.

18 Claims, 2 Drawing Sheets

OPAQUE GOGGLES HAVING OPENABLE WINDOW

The present invention relates to opaque goggles having an openable window therein. The goggles are useful in dual-brain phychological studies, psychotherapy, and in general to diminish psychological distress.

BACKGROUND OF THE INVENTION

It has long been known that the two hemispheres of the human brain control different functions of the body and the psychological state of a person. Fredric Schiffer, M.D. is a pioneer in dual-brain psychological studies. He started with two pairs of ordinary goggles and modified them by taping over the left side and part of the right side of one pair and by taping over the right side and part of the left side of the other pair. This was obviously a make-shift, do-it-yourself modification of the goggles. However, it allowed Dr. Schiffer to restrict the wearer's field of view to the outer periphery of one eye or the other by merely having him or her wear one or the other pairs of the goggles. Dr. Schiffer has found that by having the subject wear one pair of the modified goggles and then the other that it is possible to independently access each hemisphere of a subject's brain in order to get an indication of the mental state of a subject. He discovered that many people experienced an increase or decrease in their psychological symptoms as a function of accessing one lobe of the brain as opposed to the other.

SUMMARY OF THE INVENTION

It is an object of the current invention to provide an improved pair of goggles that has an openable window on one side.

It is an object of the current invention to provide an improved pair of goggles that has two openable windows, one on each side.

It is a further object of the current invention to provide an improved pair of goggles in which a single window area may be reversed so that a single pair of goggles may be provided rather than two.

It is an object of the invention to provide a practical, versatile and commercial pair of such goggles.

These objects and others that will become apparent from the following specification are achieved by an improved pair of goggles capable of allowing only one eye at a time to view things peripherally, which comprises:

(a) an opaque, translucent or tinted transparent front part of the goggles which fits in front of and covers the eyes of a wearer of the goggles, said front part having at least one window through which the wearer can view things through the outer periphery of the wearer's field of vision.

(b) a cover for the window which is capable of selectively covering the window or allowing the wearer to view things, and (c) a part that allows the wearer to wear the goggles.

The improved goggles may be used in psychotherapy. I have discovered that when a subject who previously was cognitively disorganized, wears the goggles for a few minutes, the person becomes capable of functioning in a cognitively organized fashion thereafter. Experience also shows that persons with adult attention deficit disorder can be improved to the point where they can function to take a test which requires them to focus on the questions and the answers to be provided to the questions. In addition, the improved goggles of the invention may be used in applications in special education in order to improve the learning ability of children with attention deficit disorder.

BRIEF DESCRIPTION OF THE DRAWINGS

In the Figures, the same or similar parts have been given the same reference numerals.

PREFERRED EMBODIMENTS OF THE INVENTION

Figure 1:
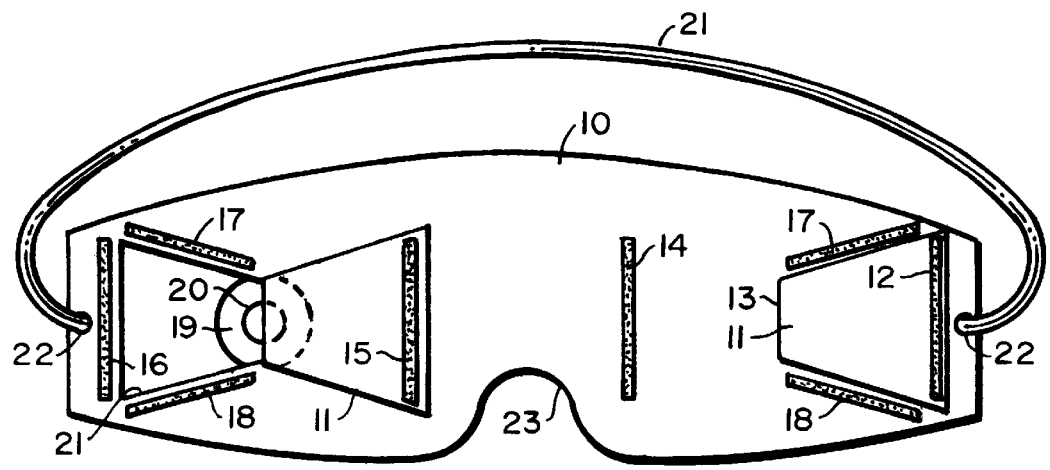
FIG. 1 is a front view of a pair of goggles as they would be seen from the vantage point of a second party viewing their wearer.
Figure 2:
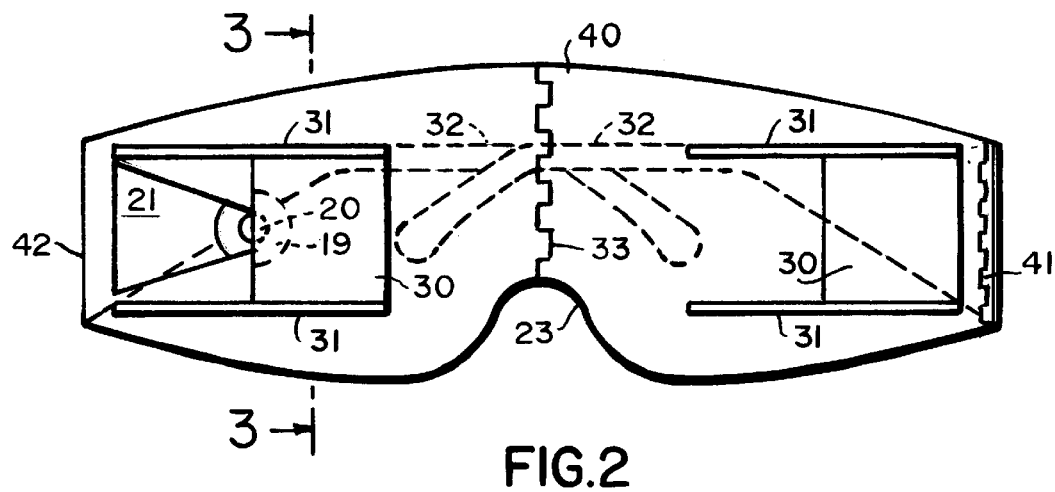
FIG. 2 illustrates an alternative sliding cover for covering the window.

FIG. 1 illustrates one embodiment of the invention which is suitable for use by children, especially in special education applications for children who have attention deficit disorder. The left side and the right side of the goggles in FIGS. 1 and 2 are in a mirror image relationship. In FIG. 1, the goggles have a front part 10 which may be made of any suitable flexible plastic material, e.g., polyethylene or polypropylene of a suitable thickness to withstand the use and abuse of the child. Front part 10 has a nose notch 23. In the left side of the illustration, cover 11 is shown in the open position. In the right side of the illustration, cover 11 is shown in the closed position. Hinge 13 may be integrally molded with front part 10 and cover 11 or may be fabricated. Along the right edge of the cover 11 is one part of hook and loop fastener (e.g., Velcro®) 15. Instead of a hook and loop fasteners, snap closures, hook-and-eye fasteners, etc. may be used. When the cover 11 is in the closed position, which is illustrated in the right side of the figure, hook and loop fastener 15 attaches to the other complementary part of the hook and loop fastener 16. In the open position, cover 11 exposes the window 21, allowing the part of the pupil 20 of the eye to view the periphery of its field of vision. Iris 19 is shown to partially indicate the eye which is not fully illustrated. One part of a hook and loop fastener 17 is above the window 21 and another part of hook and loop fastener 18 is positioned below window 21. These parts of a hook and loop fastener may be used to place colored filters over the window 21. The colored filters have the same shape as the window 21, have a slightly larger size and have the other complementary parts of the hook and loop fasteners attached in places that correspond to the placement of the parts of the hook and loop fasteners 17 and 18 over and under the window 21, thereby allowing the viewer to view the world as colored through the filter. Along the right edge of the closed cover 11 shown on the right side of FIG. 1, there is one part of a hook and loop fastener 12 which, when the cover 11 is opened, may be attached to the other complementary part of the hook and loop fastener 14. Elastic band 21 is attached, for example, by knotting its ends through eyelets 22 in the left and right of the front part 10. Instead of an elastic band 21, one end of each of two cords can be tied, one to each eyelet 22 of the front part 10, and their other ends can be tied together, thereby affixing the goggles in place of the face of the wearer. If the front part 10 has only one window, it may be switched to the other side of the goggles if the front part 10 is flexed in the other direction and worn so that its formerly outward face is now toward the face of the wearer. Reversing these goggles is therefore not as convenient as using the goggles of the invention that have two openable windows. Consequently, goggles of the invention that have two openable windows are preferred. Also preferred is a configuration of the goggles that is contoured to the user's face so that they wrap around the user's eyes thereby preventing any unwanted peripheral vision.

In FIG. 2, an alternative version of the improved goggles of the invention is illustrated. They may be made from polystyrene, polycarbonate, polyacrylate or other suitable substantially rigid plastic. However, the goggles can be made out of almost any other suitable material, e.g., metal such as aluminum or light gauge stainless steel, or fabric, which may be vacuum-formed. Again, front part 40 has window 21 therein, which allows pupil 20 to view through its periphery vision. Cover 30, shown on the right in the closed position is shown in the open position in the left part of the figure. Side frames 32 are attached to the left and right sides of front part 40. Two alternative ways of attaching the side frames 32 to the front part 40 are illustrates. One way is to have a fabricated hinge 41 connecting front part 40 and side frames 32. The other way is to have either a rigid connection or an integral molded hinge between the side frame 32 and the front part 40 along line 42. An optional feature that may be included for the traveller is hinge 32 which allows the goggles to be folded up into a compact package for stowing in the wearer's pocket.

Figure 3:
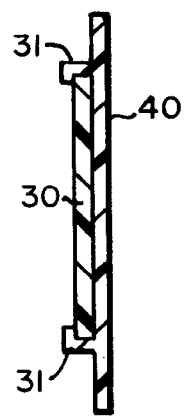
FIG. 3 is a cross section of the front part of the goggles shown in FIG. 2 taken along with view line 3—3.

FIG. 3 is a cross section of the front part of the goggles shown in FIG. 2 taken along the view line 3—3. Front part 40 has L-shaped channels 31 through which the cover 30 may be slid back and forth. When the window 21 is open, appropriately shaped and sized color filters may be slid into the channels 31.

Figure 4:
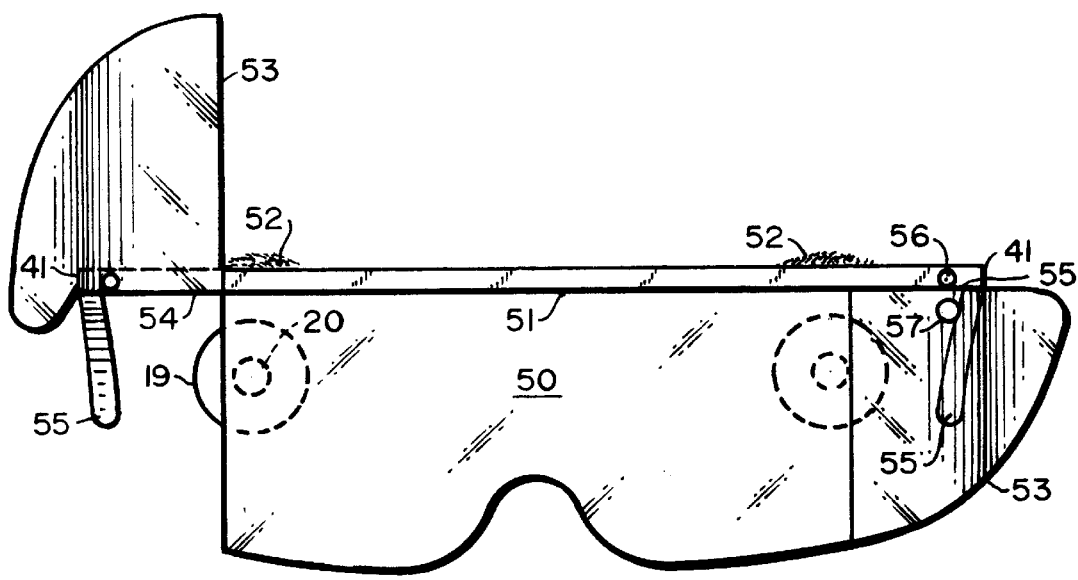
FIG. 4 illustrates an alternative set of goggles.

FIG. 4 illustrates an alternative set of goggles which comprises a front frame 51, which when worn is set so that it is approximately in front of a wearer's eyebrows 52. An opaque, translucent or tinted transparent front part 50 of the goggles is attached at its top to the front frame 51 and fits in front of and covers the eyes of a wearer of the goggles. The front part 51 has at least one section 53 hinged 54 at its top and extending from a point at least fifty percent of the distance from the wearer's pupil 20 to an outer edge of the iris 19, to the outside edge of the goggles. When the section 53 is in its up position as shown on the left of FIG. 4, the wearer can view things by the outer periphery of the wearer's field of vision. The goggles have a means for allowing the wearer to wear the goggles, preferably, side frames 55. On the right of FIG. 4, the hinged section 53 is shown in the down position. Preferably, the front part of the goggles are generally contoured to the wearer's face. The hinged section 53 preferably has a means, e.g., a snap fastener with a female part 56 and a male part 57, for maintaining section 53 in an up position. The goggles may be made of plastic. e.g., a polyethylene, polypropylene, polyester, polystyrene, polycarbonate, or polyacrylate.

The foregoing specification and drawings have thus described and illustrated improved goggles having an openable window which fulfills all the objects and advantages sought therefor. Many changes, modifications, variations and other uses and applications of the subject invention will, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. An improved pair of goggles capable of allowing one eye at a time to view things peripherally, which comprises:

(a) an opaque, translucent or tinted transparent front part of the goggles which fits in front of and covers the eyes of a wearer of the goggles, said front part having a center and two outside edges, said front part including a window, on at least one side thereof, through which the wearer can view things by the outer side periphery of the wearer's field of vision, said window extending outward from a point, when the goggles are worn by a wearer, no closer to the center than the wearer's pupil, on one side, at least to a point near the outside edge, on the same one side;

(b) a cover for the window which is selectively moveable between a position covering the window, blocking the wearer's view through the window, and a position not covering the window allowing the wearer to view things through the window; and (c) a means for allowing the wearer to wear the goggles.

2. An improved pair of goggles as claimed in claim 1, in which the front part of the goggles are generally contoured to the wearer's face.

3. An improved pair of goggles as claimed in claim 1, in which the goggles have a hinged cover and a means for maintaining the cover in either an open or closed position.

4. An improved pair of goggles as claimed in claim 1, in which the goggles have means for attaching color filters over an open window.

5. An improved pair of goggles as claimed in claim 1, in which the goggles have a sliding cover and a means for maintaining the cover in either an open or closed position.

6. An improved pair of goggles as claimed in claim 1, in which the goggles are flexible.

7. An improved pair of goggles as claimed in claim 1, in which the goggles are made of plastic, metal or fabric.

8. An improved pair of goggles as claimed in claim 7, wherein the plastic is a polyethylene, polypropylene, polyester, polystyrene, polycarbonate, or polyacrylate.

9. An improved pair of goggles as claimed in claim 1, in which the goggles have an elastic band as the means for allowing the wearer to wear the goggles.

10. An improved pair of goggles as claimed in claim 1, in which the goggles have side frames as the means for allowing the wearer to wear the goggles.

11. An improved pair of goggles capable of allowing one eye at a time to view things peripherally, which comprises:

(a) a front frame, which when worn is set so that it is approximately in front of a wearer's eyebrow;

(b) an opaque, translucent or tinted transparent front part of the goggles which is attached at it stop to the frame and fits in front of and covers the eyes of a wearer of the goggles, said front part having a center and two outside edges, said front part including a section, on at least one side thereof, hinged at its top and extending outward from a point, when the goggles are worn by a wearer, no closer to the center than the wearer's pupil, on one side, at least to a point near the outside edge, on the same one side, and through which, when the section is in its up position, the wearer can view things by the outer side periphery of the wearer's field of vision, and (d) a means for allowing the wearer to wear the goggles.

12. An improved pair of goggles as claimed in claim 11, in which the front part of the goggles are generally contoured to the wearer's face.

13. An improved pair of goggles as claimed in claim 11, in which the hinged section has a means for maintaining the section in either an open or closed position.

14. An improved pair of goggles as claimed in claim 11, in which the goggles are flexible.

15. An improved pair of goggles as claimed in claim 11, in which the goggles are made of plastic, metal or fabric.

16. An improved pair of goggles as claimed in claim 15, wherein the plastic is a polyethylene, polypropylene, polyester, polystyrene, polycarbonate, or polyacrylate.

17. An improved pair of goggles as claimed in claim 11, in which the goggles have an elastic band as the means for allowing the wearer to wear the goggles.

18. An improved pair of goggles as claimed in claim 11, in which the goggles have side frames as the means for allowing the wearer to wear the goggles.

\* \* \* \* \*